United States Patent [19]  [11] 4,414,327
Hammond et al.  [45] Nov. 8, 1983

[54] METHOD FOR THE ESTIMATION OF N-ACYLATED PRIMARY AROMATIC AMINES

[75] Inventors: Peter M. Hammond, Melton Mowbray; Christopher P. Price, Stapleford; Michael D. Scawen; Anthony Atkinson, both of Salisbury, all of England

[73] Assignee: Public Health Laboratory Service Board, London, England

[21] Appl. No.: 326,276

[22] Filed: Dec. 1, 1981

[30] Foreign Application Priority Data

Dec. 2, 1980 [GB] United Kingdom ............... 8038634

[51] Int. Cl.$^3$ .......................... C12Q 1/34; C12R 1/39; C12R 1/40
[52] U.S. Cl. ...................................... 435/18; 435/805; 435/810; 435/876; 435/877
[58] Field of Search .................... 435/18, 4, 810, 805, 435/876, 877

[56] References Cited

U.S. PATENT DOCUMENTS 3,986,931 10/1976 Bernt et al. ............................ 435/4
4,336,331 6/1982 Nagasawa et al. .................. 435/24

FOREIGN PATENT DOCUMENTS 55-99198 7/1980 Japan ..................................... 435/4

OTHER PUBLICATIONS

Hammond et al., The Lancet, 1(8216), 391–392 (1981).

*Primary Examiner*—Esther M. Kepplinger
*Attorney, Agent, or Firm*—Cushman, Darby & Cushman

[57] ABSTRACT

A method for the estimation of an anilide in which the anilide is first hydrolyzed enzymatically to an aniline and then the quantity of the aniline produced is estimated spectrophotometrically preferably colorimetrically.

The hydrolysis of the anilide may be catalyzed by any enzyme of the type, EC 3.5.1.13, known as aryl acylamidases. Preferably enzymes isolated from the cells of *Pseudomonas fluorescens* ATCC 39005 or *Pseudomonas putida* ATCC 39004 are employed.

The aniline may be analyzed, for example, by conversion to an indamine, an indophenol or an indoaniline, followed by colorimetric analysis of the colored quinone-type compound produced. This conversion may take place in the presence of an oxidizing agent, such as a copper (II) salt, and/or a base, such as ammonia.

A diagnostic kit to allow the routine use of the above method is also provided. In one embodiment of the kit, it comprises, (a) an aryl acylamidase, in solution or on a solid support,
(b) an organic compound suitable for the conversion of the aniline to an indamine, an indophenol or an indoaniline, preferably in solution, and
(c) a base, preferably in solution.

The kit may further comprise an oxidizing agent, again preferably in solution.

The above method of analysis and diagnostic kit may be particularly useful in the estimation of anilide drugs, such as paracetamol, dissolved in biological fluids.

46 Claims, 1 Drawing Figure

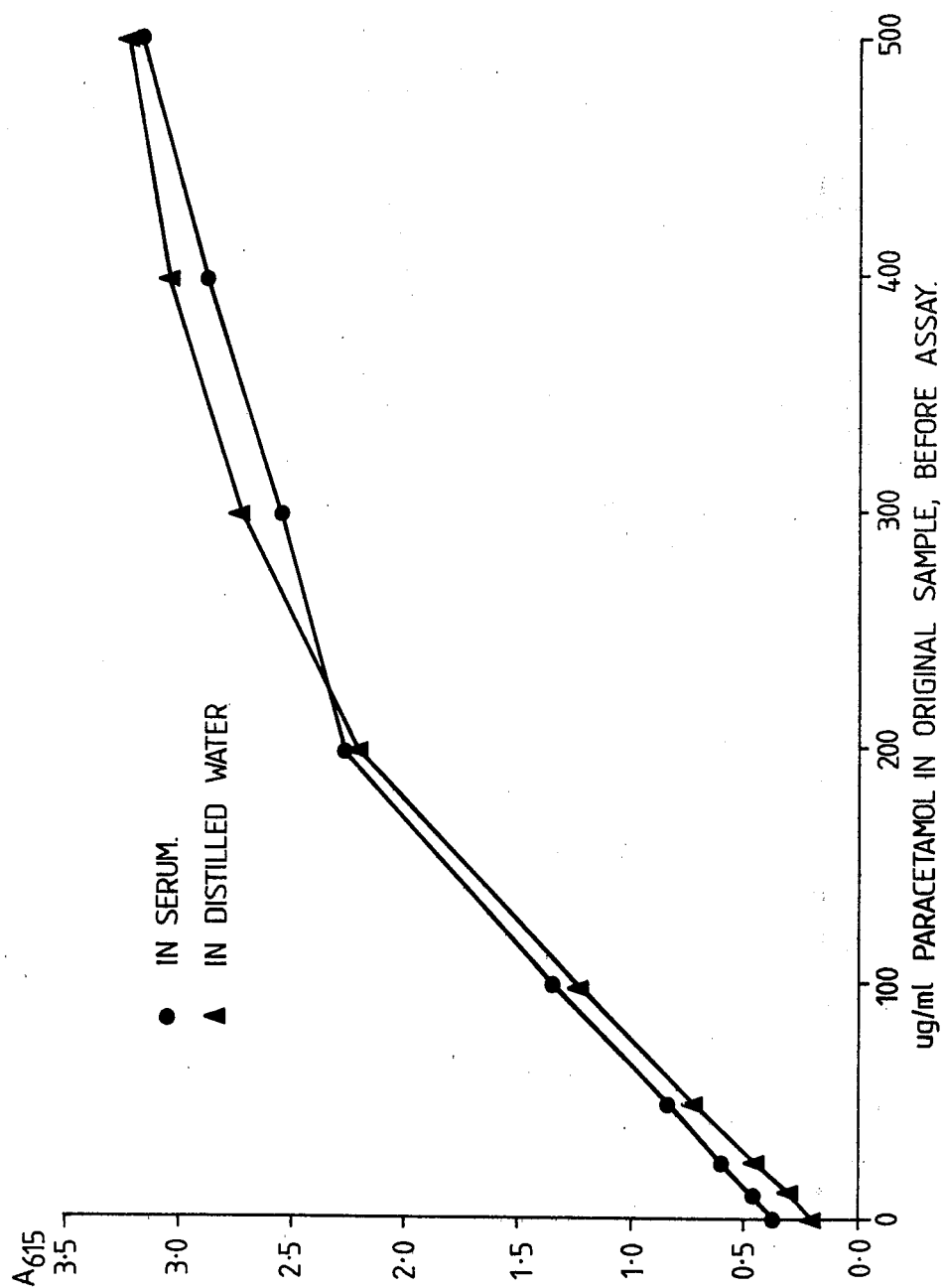

METHOD FOR THE ESTIMATION OF N-ACYLATED PRIMARY AROMATIC AMINES

This invention relates to a method for the estimation of N-acylated primary aromatic amines (anilides), for example the drugs paracetamol or phenacetin, and to a diagnostic kit for enabling said method to be performed routinely.

A number of methods for estimating the amount of an anilide, especially an N-acyl-4-substituted aniline, in a given sample, solution or mixture are known. For example, N-acetyl-4-hydroxyaniline (paracetamol) can be reacted with the violet coloured dye 2,2-diphenyl-1-picrylhydrazyl to give a yellow solution, which is then analysed colorimetrically (J. H. Routh, et al., *Clinical Chemistry* (1968), 14 882). This procedure involves an organic solvent extraction, followed by heating for 1 hour at 60° C.

Alternatively the anilide (typically N-acyl-4-hydroxyaniline) is hydrolysed to the primary aromatic aime (the aniline) by N HCl for 1 hour at 100° C. (S. L. Tompsett, *Ann. Clin. Biochem.*, (1969), 6, 81) or 0.3 N perchloric acid for 15 minutes at 135° C. (under pressure) or 40 minutes at 100° C. (G. S. Wilkinson, *Ann. clin. Biochem.*, (1976), 13, 435), followed by the formation and estimation of an indophenol with o-cresol. Perchloric acid is preferred due to the shorter hydrolysis and more rapid colour formation with o-cresol.

In another method of N-acetyl-4-hydroxyaniline estimation, the phenyl ring of the anilide is first nitrosated, using nitrous acid or a nitrous acid generating system and then a coloured product is obtained by addition of alkali to the nitroso derivative, (J. P. Glynn, et al., *Lancet*, (1975) 1, 1147).

There is a requirement to estimate the level of anilides, especially the drugs, paracetamol (N-acetyl-4-hydroxyaniline) and phenacetin (N-acetyl-4-ethoxyaniline), in biological fluids. In such cases, and especially when a patient is suffering from a drug overdose, it is important that the drug level may be ascertained in good time so that an antidote may, if necessary, be administered. Although the above methods meet this requirement to a greater or lesser extent they have the disadvantages that they require one or more of the following steps, organic solvent extraction, treatment with strong (HCl, HClO$_4$) or unstable (HNO$_2$) mineral acids, or heating at high temperature.

It is the aim of the present invention to provide a method for the estimation of anilides which requires none of these steps yet still produces an anilide level estimation quickly enough to allow the method to be used in the determination of drug levels in the biological fluids of suspected overdose patients.

According to the present invention there is provided a method for the estimation of an anilide comprising:
(a) enzymatically hydrolysing the anilide to an aniline, and
(b) estimating the quantity of said aniline spectrophotometrically.

Preferably the aniline is estimated colormetrically.

The hydrolysis of the anilide may be catalysed by any suitable enzyme of the type, defined as group EC 3.5.1.13 and named as aryl acylamidase by the International Union of Biochemistry (Enzyme Nomenclature 1978, Academic Press, New York, 1979), which hydrolyses anilides to anilines plus fatty acids. Preferably the enzyme is an aryl acylamidase isolated from cells of one of the strains *Pseudomonas fluorescens* NCIB 11615, deposited at the National Collection of Industrial Bacteria, Aberdeen, Scotland on 8th October 1980 (equivalent to *Pseudomonas fluorescens* ATCC 39005. deposited at the American Type Culture Collection. Md. on Nov. 19, 1981), or aryl acylamidase producing mutants or variants thereof, or *Pseudomonas putida* NCIB 11616 deposited at NCIB on 8th Oct. 1980 (equivalent to *Pseudomonas putida* ATCC 39004 deposited at ATCC on Nov. 19, 1981) or aryl acylamidase producing mutants or variants thereof. Preferably the aryl acylamidase is isolated from these strains by the process described in copending U.K. patent application No. 8,038,633 (Agents reference JX/5886/01). In this process the strains are cultured in a culture medium in which the strains are capable of producing aryl acylamidase and then the cell material is collected. Preferably the collected cell material is then disrupted, generally by the enzyme treatment of the cells with lysozyme-EDTA, and the aryl acylamidase is separated from the cell debris and the other cell constituents by a process including the steps of precipitation, hydrophobic and ion exchange chromatography and gel filtration. Preferably the culture medium is a complex medium containing an N-acylaniline, especially N-acetylaniline.

Mutant or variant strains of *Pseudomonas fluorescens* NCIB 11615 (ATCC 39005) or *Pseudomonas putida* NCIB 11616 (ATCC 39004) may be obtained by environmental selection pressure techniques (stripculture), by UV irradiation or the use of mutagenic chemicals, etc. They may also be produced by genetic manipulation techniques, for example by the transfer of plasmid DNA to a multicopy host or by the excision of the chromosomal genes coding for aryl acylamidase from the cells of the aryl acylamidase producing bacteria, followed by cloning of said genes into a suitable vector molecule.

The enzymatic hydrolysis is shown in Equation A, anilide 1, ($R_1$=H or an acyl group, $R_2$=an acyl group, $R_3$=one or more ortho-, meta- or para-substituents) being hydrolysed to aniline 2, ($R_3$=as above).

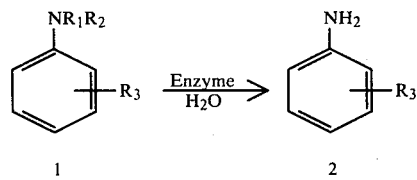

Among the advantages of enzyme catalysed hydrolysis of the N-acyl bond over the analogous acid catalysed reactions are that,
(1) the enzyme catalysed reaction generally takes place very quickly (1-2 minutes) under conditions of normal temperature and pressure without hazardous reagents.
(2) such an enzyme catalysed hydrolysis generally shows a higher degree of specificity, which can relieve the need for tedious extraction or fractionation procedure. This specifity may be particularly important when the free anilide is in admixture with a number of other compounds which may, under rigorous hydrolysing conditions, afford a free aniline. Such an additional aniline would interfere with the analysis step and lead to a spuriously high reading. Thus the process of this invention may be particularly useful in estimating the amount of anilide present in biological fluids. In particular the level of such drugs as paracetamol and phenacetin in such fluids may be profitably investigated using this method.

The enzymatic hydrolysis is generally performed in substantially aqueous solution. In order to store the enzyme over a long period it is preferably stored at reduced temperatures (between about 10° and −20° C.) in the presence of a stabilising agent, for example glycerol. In a preferred embodiment of the method of this invention the enzyme is dissolved in a solution of aqueous glycerol, said solution containing between about 10–70% (v/v) of glycerol.

The aniline derived from the enzymatic hydrolysis may be estimated by any suitable method. For example readily oxidisable anilines such as 3 (X=NH₂ or OH) may be reacted with readily reducible

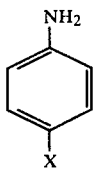
3 compounds, such as the tetrazolium dyes, especially 3-(4,5-dimethylthiazolyl)-2,5-diphenyl tetrazolium bromide (MTT), to form coloured complexes which may then be analysed colorimetrically.

Alternatively, such readily oxidisable anilines may be reacted with metal ions which have more than one oxidation state and which undergo a colour change when converted from one state to another. Thus, addition of 4-hydroxyaniline to a yellow solution of ferric chloride gives a blue solution of ferrous chloride, whilst addition to cupric sulphate gives a black ppt of cuprous sulphate. Alternatively, addition of 4-hydroxyaniline to a solution of ferric ions followed by the addition of the solution of ferrous ions obtained to a solution of ferricyanide ions gives an intense blue solution. In all of these cases the coloured solution may subsequently be analysed colorimetrically.

Preferably, however, the anilines derived from the enzymatic hydrolysis of the anilides are estimated by conversion to an indamine, an indophenol or an indoaniline, followed by spectrophotometric, preferably colorimetric analysis. The unsubstituted forms of the indamine (4), indophenol (5) and indoaniline (6) are as follows.

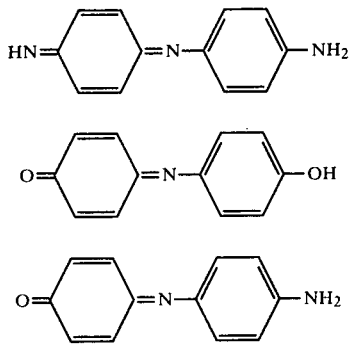

The organic compounds chosen to convert the aniline to an indamine, an indophenol or an indoaniline will depend on the structure of the aniline to be converted.

Thus, if the aniline is of structure 7 (R=para—NH₂ or para—OH),

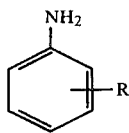
7 then the preferred organic compound will be of structure 3 (X=NH₂ or OH).

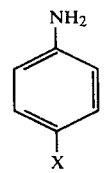
3

On the other hand, if the aniline is of structure 3, then the preferred organic compound will be of structure 8 (at least one of R₂ and R₃=an ortho- or para-directing substituent group which is not an alkyl or halogen group. The benzene ring may be further substituted by any suitable substituent groups).

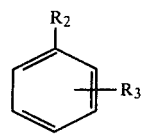
8

Thus in the analysis of aniline by this process, an organic compound of structure 3, (X=NH₂ or OH) would preferably be used to form a coloured indamine or indoaniline derivative. By contrast, analysis of 4-hydroxyaniline may be performed by initial reaction with for example a primary, secondary or tertiary aryl amine (8, R₂=NH₂, NH(Alkyl) or N(Alkyl)₂ respectively), preferably a phenylenediamine (8), R₂=NH₂, R₃=NH₂), especially meta phenylenediamine (8, R₂=NH₂, R₃=meta—NH₂), to form an indoaniline or indamine. Preferably, however, analysis of 4-hydroxyaniline may be performed by initial reaction with a phenol (8 R₂=OH) or a phenolic ether (8, R₂=O—Alkyl), preferably a cresol (8, R₂=OH, R₃=CH₃), especially ortho-cresol (8, R₂=OH, R₃=ortho—CH₃) to form an indophenol.

The conversion of the aniline to an indamine, an indophenol or an indoaniline may be performed in alcoholic or aqueous alcoholic solution. Preferably, however, the reactions take place in substantially aqueous solution. In order to proceed at a reasonable rate the reactions generally proceed at an alkaline pH, in the presence of a base, such as an alkali metal hydroxide, aborate buffer, or an alkaline solution of an organic amine, for example ethaolamine. Preferably, however the base is ammonia.

The rate of reaction, and therefore maximum colour formation, will depend on the reactants chosen, in general however maximum colour formation will not have occurred at room temperature in less than about 2 hours. In certain circumstances it may be that a faster rate of reaction (and colour formation) will be required. This may be especially true when the level of an anilide, particularly of the drugs paracetamol or phenacetin, in a biological fluid is to be estimated.

It has been found that by adding an oxidising agent such as an Fe (III), chlorate, dichromate, permanganate or, preferably Cu(II) salt to the reaction mixture the rate of conversion of the aniline to the indamine, indophenol or indoaniline is substantially enhanced. Thus addition of for example copper (II) sulphate to a mixture of 4-hydroxyaniline, ortho-cresol and ammonia leads to the quantitive formation of an indophenol at room temperature in between about 5 to 10 minutes. The same reaction, in the absence of a copper (II) salt has not proceeded to completion in 2 hours. This modification also allows the concentration of ammonia in the assay to be reduced. In the case of 4-hydroxyaniline analysis this precludes interference in the colorimetric analysis by the violet colour formed by 4-hydroxyaniline in the presence of high levels of ammonia.

The wavelength at which the colorimetric analysis of the indamine, indophenol or indoaniline solution is conducted will depend upon the colour of the compound obtained and therefore upon its wavelength of maximum absorbance. For example, analysis of the indamine derived from 4-hydroxyaniline and meta-phenylenediamine is effected at about 630 nm, whilst that of the indophenol derived from 4-hydroxyaniline and ortho-cresol is analysed at a wavelength of about 615 nm.

The method of estimating anilides of the present invention will have many applications, however it will be particularly useful if a quick and routine method of analysis is required. The analysis may be completed in between about 10 to 15 minutes and does not require any form of extraction, the use of high temperatures and pressures or the use of corrosive mineral acids.

The present method of analysis will, however, be particularly useful in the medical field, especially in the estimation of anilides, such as drugs paracetamol and phenacetin, in biological fluids. In such biological fluids the anilide of interest may be in admixture with compounds and complexes which on rigorous hydrolysis would afford an aniline derivative. Such additional anilines would lead to interference in the analysis step and to spurious results. It is a particular advantage of the present method that the use of an enzymatic hydrolysis step followed preferably by an indamine/indophenol/indoaniline aniline analysis step leads to results for anilide level in biological fluids that correspond very closely to the results obtained for the same concentration of anilide in aqueous solutions. For example, when the same amount of N-acetyl-4-hydroxyaniline was dissolved in equal volumes of water and serum, analysis by arylacylamidase hydrolysis followed by reaction with ortho-cresol and colorimetric analysis at 615 nm led to virtually identical results for anilide concentration.

The procedure is sensitive to levels of N-acetyl-4-hydroxyaniline (paracetamol) below those of therapeutic significance and the colorimetric analysis has a linear relationship with initial paracetamol levels over the range 0-200 ug paracetamol per ml original serum sample. Levels in excess of this, which are those associated with hepatic damage, may be brought within the assay range by dilution of serum samples. As outlined above, serum does not absorb significantly at the wavelength used in the analysis of paracetamol, and none of its normal constituents interfere with the analysis.

In order to further facilitate the use of this method of analysis in a routine manner, especially by medical techniques, the invention further provides a diagnostic kit for use in the estimation of an anilide by the preferred process of the invention comprising:

(a) an enzyme suitable for the hydrolysis of the anilide to an aniline, and
(b) an organic compound suitable for the conversion of the aniline to an indamine, an indophenol or an indoaniline.

The enzyme may be retained on a solid support or, preferably, dissolved in one or more suitable solvents. The organic compound is preferably dissolved in one or more suitable solvents.

As outlined above, the enzyme may be any suitable enzyme of the type, defined as groups EC 3.5.1.13 and named as aryl acylamidase. Preferably the enzyme is an aryl acylamidase isolated from cells of one of the strains *Pseudomonas fluorescens* NCIB 11615 ATCC 39005 or aryl acylamidase producing mutants or variants thereof or *Pseudomonas putida* NCIB 11616 ATCC 39004 or aryl acylamidase producing mutants or variants thereof.

The organic compound for aniline conversion may be any having the structure 3 or 8 above. Preferably, however, the organic compound is a phenol or phenolic ether, especially a cresol, most especially ortho-cresol, or a primary, secondary or tertiary aryl amine, especially phenylenediamine, most especially meta-phenylenediamine The diagnostic kit of the present invention may further comprise an oxidising agent such as an Fe (III), a chlorate, a dichromate or a permanganate salt or preferably a copper (II) salt, particularly copper sulphate. Preferably the oxidising agent is dissolved in one or more suitable solvents. The kit may additionally comprise a base, for example an alkali metal hydroxide, a borate buffer or an alkaline solution of an organic amine for example ethanolamine. Preferably however the base is ammonia. Preferably the base is dissolved in one or more suitable solvents. In one preferred embodiment, solutions of the oxidising agent, for example a copper (II) salt, and the base, such as ammonia, may be combined, whilst in another preferred embodiment solutions of the oxidising agent for example a copper (II) salt, the base, for example ammonia, and the indamine/indophenol/indoaniline forming organic compound may be combined.

A suitable solvent for dissolving the enzyme, the aniline converting organic compound, the oxidising agent and the base may be alcohol, aqueous alcohol or preferably water. In order to retain the activity of the enzyme over long periods the enzyme's solvent preferably contains glycerol. In a particularly preferred embodiment of the diagnostic kit of this invention the enzyme is dissolved between about 10 and 70% (v/v) glycerol and between about 90 and 30% (v/v) water, most preferably in a 50% aqueous solution of glycerol, and stored at temperatures between 10° C. and −20° C.

In order to further retain the activity of the enzyme the enzyme solution may be stored at low temperature (5° to −20° C.) either with other solutions of the kit or separate therefrom.

In order to further facilitate the use of the kit of this invention, each kit may be provided with a set of instructions setting out each step of the assay procedure.

The method and kit of the present invention will now be more particularly described with reference to the FIGURE in which the absorption, at 615 mm, of indophenol, formed by enzymatic hydrolysis of paracetamol followed by addition of ortho-cresol, in the presence of ammonia, and a copper (II) salt, is plotted against initial concentration of paracetamol. In the FIGURE, results for paracetamol dissolved in water and in serum are graphically compared.

EXAMPLE 1

(a) Reagents (i) Aryl acylamidase dissolved in 50% (v/v) solution of aqueous glycerol and buffered with 0.1 M tris-HCl to pH 8.6

(ii) Ammoniacal copper sulphate solution comprising 25 cc of a 0.2% (w/v) aqueous solution of anhydrous copper sulphate mixed with 0.4 cc of 0.880 ammonia (iii) 1% (w/v) solution of aqueous ortho-cresol (b) Enzymatic hydrolysis Samples of serum (0.5 ml), each containing a different quantity of dissolved paracetamol (N-acetyl-4-hydroxyaniline), were incubated with 0.5 ml of enzyme solution (1(a)(i) above) for 5 minutes at 30° C.

Aniline determination

To 1 ml of cresol solution (1(a)(iii) above) was added 0.1 ml of ammoniacal copper sulphate solution (1(a)(ii) above). The solution was then added to 1.4 cc of water and mixed thoroughly. 0.5 cc of enzymatically hydrolysed serum solution was then added to the cresol/copper sulphate/ammonia mixture. The solution was again mixed thoroughly and allowed to stand for 5 mins. After this time the absorbance of the solution, at 615 nm, was measured against a distilled water blank.

The results for the $A_{615}$ given by various initial concentrations of paracetamol are given in tabular form in Table 1 and in graphic form in the FIGURE.

TABLE 1

| Concentration of Paracetamol in Serum (μg/ml) | $A_{615}$ |
|---|---|
| 1 | 0.35 |
| 5 | 0.40 |
| 10 | 0.45 |
| 25 | 0.60 |
| 50 | 0.85 |
| 100 | 1.36 |
| 200 | 2.25 |
| 300 | 2.56 |
| 400 | 2.87 |
| 500 | 3.18 |

EXAMPLE 2

The procedure and reagents of Example 1 were used except that the paracetamol was dissolved in water rather than serum. Results are given in Table 2 and the FIGURE.

TABLE 2

| Concentration of Paracetamol in Water (μg/ml) | $A_{615}$ |
|---|---|
| 1 | 0.21 |
| 5 | 0.25 |
| 10 | 0.30 |
| 25 | 0.46 |
| 50 | 0.73 |
| 100 | 1.23 |
| 200 | 2.22 |
| 300 | 2.73 |
| 400 | 3.04 |
| 500 | 3.19 |

Comparison of the results of Tables 1 and 2 gave a correlation coefficient of 0.9985.

EXAMPLE 3

(a) Reagents

The reagents of Example 1 were used except that the 1% (w/v) solution of aqueous ortho-cresol was replaced by a 1% (w/v) solution of aqueous meta-phenylenediamine.

(b) Enzymatic hydrolysis

Aqueous solutions of paracetamol (0.5 ml), of various concentration, were incubated with 0.5 ml of enzyme solution (1(a)(i) above) for 5 minutes at 30° C.

(c) Aniline determination

To 0.1 ml of meta-phenylenediamine solution (3(a) above) was added 0.025 ml of ammoniacal copper sulphate solution (1(a)(ii) above). The solution was then added to 0.5 ml of water and mixed thoroughly, 0.4 ml of the enzymatically hydrolysed aqueous solution of paracetamol was then added to the phenylenediamine/copper sulphate/ammonia mixture. The solution was again mixed thoroughly and allowed to stand for 10 mins. After this time the absorbance of the solution, at 630 nm, was measured against a distilled water blank.

The results for $A_{630}$ given by various initial concentrations of paracetamol solution are given in Table 3.

TABLE 3

| Concentration of Paracetamol in Water (μg/ml) | Concentration of 4-hydroxyaniline (assuming 100% hydrolysis of paracetamol) μg/ml | $A_{630}$ |
|---|---|---|
| 0 | 0 | 0.20 |
| 14 | 10 | 0.44 |
| 34.5 | 25 | 0.93 |
| 68.5 | 49.5 | 1.52 |
| 328 | 237.5 | 2.67 |
| 635 | 455 | 2.67 |

EXAMPLE 4

A solution containing 1.0 ml 1% (v/v) ortho cresol, 1.0 ml 0.4 M ammonia, 0.3 ml aqueous 4-hydroxyaniline (concn 1 mg ml$^{-1}$) and 0.7 ml water was mixed rapidly and the development of the blue colour was monitored colorimetrically at 615 mm. The results for colour formation against time are given in Table 4.

TABLE 4

| Time (mins) | $A_{615}$ |
|---|---|
| 0 | 0.00 |
| 2 | 0.85 |
| 4 | 1.76 |
| 6 | 2.40 |
| 8 | 2.84 |
| 10 | 3.02 |

EXAMPLE 5

(A)

(i) A solution containing 1% (w/v) aqueous ortho-cresol (2.4 ml) and aqueous 4-hydroxyaniline (0.5 ml, concn 0.1 mg ml$^{-1}$) was made up. To this was added an aqueous alkaline salt solution (0.1 ml), made up from 0.2% (w/v) CuSO$_4$ (10 ml) and 0.880 NH$_3$ (0.16 ml). The solutions were mixed rapidly and the rate of colour formation was estimated qualitatively.

(ii) A solution containing 1% (w/v) aqueous ortho-cresol (2.4 ml) and aqueous 4-hydroxyaniline (0.5 ml, concn 0.1 mg ml$^{-1}$) was made up. To this was added an aqueous solution of ammonia (0.1 ml), made up from H$_2$O (10 ml) and 0.880 NH$_3$ (0.16 ml). The solutions were mixed rapidly and the rate of colour formation was estimated qualitatively.

(iii) A solution containing 1% (w/v) aqueous ortho-cresol (2.4 ml) and aqueous 4-hydroxyaniline (0.5 ml, concn 0.1 mg ml$^{-1}$) was then made up. To this was added a 0.2% (w/v) aqueous solution of CuSO$_4$ (0.1 ml). The solutions were mixed rapidly and the rate of colour formation was estimated quantitatively.

Results for (A) (i), (ii) and (iii) are given in Table 5.

(B)

(i) The procedure of Example 5A(i) was repeated except that K$_2$Cr$_2$O$_7$ replaced CuSO$_4$.
(ii) The procedure of Example 5A(ii) was repeated.
(iii) The procedure of Example 5A(iii) was repeated except that K$_2$Cr$_2$O$_7$ replaced CuSO$_4$. Results for B(i), (ii) and (iii) are given in Table 5.

(C)

(i) The procedure of Example 5A(i) was repeated except that FeCl$_3$6H$_2$O replaced CuSO$_4$.
(ii) The procedure of Example 5A(ii) was repeated.
(iii) The procedure of Example 5A(iii) was repeated except that FeCl$_3$6H$_2$O replaced CuSO$_4$. Results for C (i), (ii) and (iii) are given in Table 5.

(D)

(i) The procedure of Example 5A(i) was repeated except that KMnO$_4$ replaced CuSO$_4$.
(ii) The procedure of Example 5A(ii) was repeated.
(iii) The procedure of Example 5a(iii) was repeated except that KMnO$_4$ replaced CuSO$_4$.
Results for (D) (i), (ii) and (iii) are given in Table 5.

TABLE 5

| Mixture | Colour of solution | Rate of colour formation |
|---|---|---|
| A(i) | Blue | Rapid |
| A(ii) | Blue | Slow |
| A(iii) | Brown/Pink | Slow |
| B(i) | Green then Blue | Slow |
| B(ii) | Blue | Slow |
| B(iii) | Brown/Pink | Slow |
| C(i) | Blue | Slow |
| C(ii) | Blue | Slow |
| C(iii) | Brown/Pink | Slow |
| D(i) | Blue | Rapid |
| D(ii) | Blue | Slow |
| D(iii) | Blue | Moderate |

Note:
(1) Cu$^{2+}$ and MnO$_4$$^{2-}$ ions have a positive influence on the rate of colour formation when the reaction is performed in alkaline (ammoniacal) solution. Cr$_2$O$_7$$^{2-}$ and Fe$^{3+}$ ions do not have a positive influence in alkaline solution, however if Cr$_2$O$_7$$^{2-}$ or Fe$^{3+}$ ions are mixed with 4-hydroxyaniline and ortho-cresol at neutral pH, and ammonia is subsequently added, the blue colour forms immediately.
(2) Permanganates are known to be less stable than Copper salts in solution. Over a period of time manganese dioxide is formed from KMnO$_4$.

EXAMPLE 6

A qualitative colorimetric estimation of 4-hydroxyaniline was performed using 3-(4,5-dimethylthiazolyl-2)-2,5-diphenyl tetrazolium bromide (MTT) at various pH.

To 0.5 ml samples of MTT (concentration 1 mg/ml) was added various amounts of 4-hydroxyaniline (concentration 1 mg/ml). The solution was buffered to pH 5.0 using citrate buffer and the reaction allowed to proceed for 10 mins. The solution was then inspected and the colour noted. Results are given in Table 6.

EXAMPLES 7–9

The procedure of Example 6 was repeated except that the solutions were buffered to pH 7.6, 8.6 and 10.5 respectively using potassium phosphate, tris and borate buffers. Results are given in Table 6.

TABLE 6

| Example No | pH | Volume of 4-hydroxyaniline solution added (ml) | Colour of Solution after 10 mins |
|---|---|---|---|
| 6 | 5.0 | 0 | Yellow |
|  | 5.0 | 0.1 | Yellow |
|  | 5.0 | 0.5 | Yellow |
|  | 5.0 | Excess | Green |
| 7 | 7.6 | 0 | Yellow |
|  | 7.6 | 0.1 | Yellow |
|  | 7.6 | 0.5 | Green |
|  | 7.6 | Excess | Deep Purple |
| 8 | 8.6 | 0 | Yellow |
|  | 8.6 | 0.1 | Blue |
|  | 8.6 | 0.5 | Deep Purple |
|  | 8.6 | Excess | Deep Purple |
| 9 | 10.5 | 0 | Yellow |
|  | 10.5 | 0.1 | Deep Purple |
|  | 10.5 | 0.5 | Deep Purple |
|  | 10.5 | Excess | Deep Purple |

EXAMPLES 10–13

The procedure of Examples 6–9 was repeated except that Iodonitrotetrazolium violet replaced MTT. Results are given in Table 7.

TABLE 7

| Example No | pH | Volume of 4-hydroxyaniline solution added (ml) | Colour of solution after 10 mins |
|---|---|---|---|
| 10 | 5.0 | 0 | Clear |
|  | 5.0 | 0.1 | Clear |
|  | 5.0 | 0.5 | Clear |
|  | 5.0 | Excess | Clear |
| 11 | 7.6 | 0 | Clear |
|  | 7.6 | 0.1 | Clear |
|  | 7.6 | 0.5 | Faint Pink |
|  | 7.6 | Excess | Pink |
| 12 | 8.6 | 0 | Clear |
|  | 8.6 | 0.1 | Clear |
|  | 8.6 | 0.5 | Pink |
|  | 8.6 | Excess | Red |
| 13 | 10.5 | 0 | Clear |
|  | 10.5 | 0.1 | Red |
|  | 10.5 | 0.5 | Red |
|  | 10.5 | Excess | Red |

EXAMPLE 14

A qualitative colorimetric estimation of 4-hydroxyaniline was performed using the "Turnbull's Blue" test.

An aqueous solution of 4-hydroxyaniline was added to an aqueous solution of ferric chloride and potassium hexacyanoferrate. A deep blue colour (Turnbull's Blue) developed almost immediately.

This test is sensitive to concentrations of 10 µg ml$^{-1}$ of 4-hydroxyaniline in water.

EXAMPLES 15–21

Quantitative colorimetric estimations of 4-hydroxyaniline were performed using the "Formazon" test.

A known amount of an aqueous solution of 4-hydroxyaniline (Concn 1 mg ml$^{-1}$) was added to an aqueous solution of iodonitrotetra zolium violet (INT, 1 ml, Concn 1 mg ml$^{-1}$).

The volume of this solution was then made up to 3 ml by the addition of borate buffer (pH 10.5). The solution was then rapidly mixed and after 5 mins the absorbance of the solution at 580 nm was measured colorimetrically against a distilled water blank. Results are given in Table 8.

TABLE 8

| Example | Volume of 4-hydroxyaniline (ml) | A580 after 5 mins |
|---|---|---|
| Control | 0 | 0.01 |
| 15 | 0.01 | 0.125 |
| 16 | 0.025 | 0.542 |
| 17 | 0.05 | 0.987 |
| 18 | 0.075 | 1.604 |
| 19 | 0.1 | 2.075 |
| 20 | 0.2 | 00 |
| 21 | 0.4 | 00 |

EXAMPLE 22-30

Quantitative colorimetric estimates of 4-hydroxyaniline were performed using a second "Formazan" test.

A known amount of an aqueous solution of 4-hydroxyaniline (Concn 1 mg ml$^{-1}$) was added to an aqueous solution of tetranitroblue tetrazolium (TNBT, 1 ml, Concn 1 mg ml$^{-1}$). The volume of this solution was then made up to 3 ml by the addition of borate buffer (pH 10.5). The solution was then rapidly mixed and after 10 mins the absorbance of the solution at 550 nm was measured colorimetrically against a distilled water blank. Results are given in Table 9.

TABLE 9

| Example | Volume of 4-hydroxyaniline (ml) | A550 after 10 min |
|---|---|---|
| Control | 0 | 0.007 |
| 22 | 0.005 | 0.209 |
| 23 | 0.01 | 0.422 |
| 24 | 0.02 | 0.835 |
| 25 | 0.03 | 1.244 |
| 26 | 0.04 | 1.611 |
| 27 | 0.05 | 2.042 |
| 28 | 0.075 | 2.837 |
| 29 | 0.1 | 3.147 |
| 30 | 0.2 | 3.222 |

EXAMPLES 31-39

Quantitative colorimetric estimations of 4-hydroxyaniline were performed using a third "Formazan" test.

A known amount of an aqueous solution of 4-hydroxyaniline (Concn 1 mg ml$^{-1}$) was added to an aqueous solution of MTT (1 ml, Concn 1 mg ml$^{-1}$). The volume of this solution was then made up to 3 ml by the addition of borate buffer (pH 10.5). The solution was then rapidly mixed and after 5 mins the absorbance of the solution at 635 nm was measured colorimetrically against a distilled water blank.

Results are given in Table 10.

TABLE 10

| Example | Volume of 4-hydroxyaniline (ml) | A635 after 5 min |
|---|---|---|
| Control | 0 | 0.002 |
| 31 | 0.01 | 0.231 |
| 32 | 0.025 | 0.642 |
| 33 | 0.05 | 1.314 |

TABLE 10-continued

| Example | Volume of 4-hydroxyaniline (ml) | A635 after 5 min |
|---|---|---|
| 34 | 0.075 | 1.795 |
| 35 | 0.1 | 2.211 |
| 36 | 0.2 | 3.110 |
| 37 | 0.3 | 3.230 |
| 38 | 0.4 | 3.290 |
| 39 | 0.5 | 3.402 |

EXAMPLE 40

Procedure suitable for a large number of paracetamol assays.

(a) Reagents (i) Aryl acylamidase dissolved in 50% (v/v) solution of aqueous glycerol and buffered with 0.1 M tris-HCl to pH 8.6.

(ii) A colour reagent prepared by mixing 1% (w/v) aqueous ortho-cresol (100 ml), distilled water (140 ml) and an ammoniacal copper sulphate solution (10 ml) made up from 0.2% (w/v) aqueous CuSO$_4$ (25 ml) and 0.880 NH$_3$ (0.4 ml).

(b) Enzymatic hydrolysis

Undiluted serum sample (0.1 ml) was incubated with enzyme solution (40 (a) (i) above, 0.1 ml) and 0.1 M tris-HCl buffer (pH 8.6, 0.8 ml) for 5 min at 30° C.

(c) Aniline determination

To 0.5 ml of the enzymatically hydrolysed serum solution (40 (b) above) was added 2.5 ml of the colour reagent (40 (a) (ii) above). The solution was then mixed thoroughly and allowed to stand for 3 mins. After this time the absorbance of the solution, at 615 nm, was measured against a serum blank.

(d) Calibration graph and linearity

A calibration graph was constructed using human serum spiked with accurately known levels of paracetamol. These samples were treated as in the above protocol and a calibration graph of absorbance (615 nm) versus μg/ml paracetamol in the original serum sample was plotted. This allows the direct reading of unknown samples from the graph in μg paracetamol per ml serum.

EXAMPLES 41-55

Measurement of the level of paracetamol in the serum samples of human patients.

(a) Reagents

The reagents of Example 1 were employed.

(b) Enzymatic hydrolysis

Undiluted serum sample (0.1 ml) was incubated with enzyme solution (1 (a) (i) above, 0.1 ml) and 0.1 M tris-HCl buffer (pH 8.6, 0.8 ml) for 5 mins at 30° C.

(c) Aniline determination by colorimetric analysis

To 0.5 ml of the enzymatically hydrolysed serum solution (b above) was added 1% ortho-cresol (1 (a) (iii) above, 1.0 ml), ammoniacal copper sulphate solution (1 (a) (ii), 0.1 ml) and distilled water (1.4 ml). The solution was then mixed thoroughly and allowed to stand for 3 min. After this time the absorbance of the solution, at 615 nm, was measured against a serum blank.

(d) GLC aniline determination

The level of paracetamol in the undiluted serum sample was measured by gas liquid chromatography using the method of Huggett et al, *J Chromatogr*, 1981, 209, 67.

The level of paracetamol in each sample, measured by both the present colorimetric and the glc method is given in Table 11.

TABLE 11

| | Paracetamol in serum ($\mu$g ml$^{-1}$) | |
|---|---|---|
| Example | Enzyme/Colorimetric | GLC |
| 41 | 196 | 197 |
| 42 | 85 | 97 |
| 43 | 166 | 185 |
| 44 | 29 | 34 |
| 45 | 7 | 2 |
| 46 | 5 | 3 |
| 47 | 20 | 22 |
| 48 | 91 | 99 |
| 49 | 155 | 170 |
| 50 | 299 | 327 |
| 51 | 119 | 131 |
| 52 | 22 | 22 |
| 53 | 148 | 155 |
| 54 | 223 | 212 |
| 55 | 345 | 334 |

We claim:

1. In a method for the estimation of an anilide (N-acylated primary aromatic amine) comprising:
   (a) hydrolysing the anilide to an aniline, and
   (b) estimating the quantity of said aniline spectrophotometrically,
wherein the improvement comprises conducting step (a) above in the presence of an aryl acylamidase enzyme defined as group EC3.5.1.13, said enzyme being able to catalyse the hydrolysis of the anilide to the aniline.

2. A method according to claim 1 wherein the enzyme is an aryl acylamidase, EC 3.5.1.13, isolated from *Pseudomonas fluorescens* ATCC 39005 or aryl acylamidase producing mutants or variants thereof, or *Pseudomonas putida* ATCC 39004 or aryl acylamidase producing mutants or variants thereof.

3. A method according to claim 1 wherein the quantity of said aniline is estimated by:
   (a) converting the aniline to a substance selected from the group consisting of an indamine, an indophenol and an indoaniline, and
   (b) estimating the quantity of said indamine, indophenol or indoaniline spectrophotometrically.

4. A method according to claim 3 wherein the conversion of the aniline to the indamine, indophenol or indaniline is effected in the presence of an oxidising agent.

5. A method according to claim 4 wherein the oxidising agent comprises a copper (II) salt.

6. A method according to claim 4 wherein the oxidising agent comprises a salt selected from the group consisting of an Fe (III), a chromate, a dichromate and a permanganate salt.

7. A method according to claim 3 wherein the conversion of the aniline to the indamine, indophenol or indoaniline is effected in the presence of a base.

8. A method according to claim 7 wherein the base comprises ammonia.

9. A method according to claim 8 wherein the ammonia is in the form of an aqueous solution of ammonia.

10. A method according to claim 7 wherein the base comprises a base selected from the group consisting of an alkali metal hydroxide, a borate buffer and an alkaline solution of an organic amine.

11. A method according to claim 3 wherein the conversion of the aniline to the indamine, indophenol or indoaniline is effected by reacting the aniline with a substance selected from the group consisting of a phenol and a phenolic ether.

12. A method according to claim 11 wherein the phenol or phenolic ether is cresol.

13. A method according to claim 12 wherein the phenol or phenolic ether is ortho-cresol.

14. A method according to claim 3 wherein the conversion of the aniline to the indamine, indophenol or indoaniline is effected by reacting the aniline with a substance selected from the group consisting of a primary, secondary, and tertiary aryl amine.

15. A method according to claim 14 wherein the primary, secondary or tertiary aryl amine is phenylenediamine.

16. A method according to claim 15 wherein the primary, secondary or tertiary aryl amine is meta-phenylenediamine.

17. A method according to claim 14 wherein the primary, secondary or tertiary aryl amine is para-hydroxyaniline.

18. A method according to claim 1 wherein the anilide is in a biological fluid.

19. A method according to claim 1 wherein the anilide is N-acetyl-4-hydroxyaniline.

20. A method according to claim 1 wherein the anilide is N-acetyl-4-ethoxyaniline.

21. A method according to claim 1 wherein the aniline is estimated colorimetrically.

22. A diagnostic kit for use in the estimation of an anilide by a method according to claim 1 comprising:
   (a) an aryl acylamidase enzyme, defined as EC 3.5.1.13, suitable for catalysing the hydrolysis of the anilide to an aniline, and
   (b) an organic compound suitable for the conversion of the aniline to a substance selected from the group consisting of an indamine, an indophenol and an indoaniline.

23. A diagnostic kit according to claim 22 wherein the enzyme is an aryl acylamidase, EC 3.5.1.13, isolated from cells of one of the strains *Pseudomonas fluorescens* ATCC 39005 or aryl acylamidase producing mutants or variants thereof, or *Pseudomonas putida* ATCC 39004 or aryl acylamidase producing mutants or variants thereof.

24. A diagnostic kit according to claim 22 wherein the organic compound suitable for the conversion of the aniline to an indamine, an indophenol or an indoaniline is selected from the group consisting of a phenol and a phenolic ether.

25. A diagnostic kit according to claim 24 wherein the phenol or phenolic ether is cresol.

26. A diagnostic kit according to claim 25 wherein the phenol or phenolic ether is ortho-cresol.

27. A diagnostic kit according to claim 22 wherein the organic compound suitable for the conversion of the aniline to an indamine, an indophenol or an indoaniline is selected from the group consisting of a primary, secondary and tertiary aryl amine.

28. A diagnostic kit according to claim 27 wherein the primary, secondary or tertiary aryl amine is phenylenediamine.

29. A diagnostic kit according to claim 28 wherein the primary, secondary or tertiary aryl amine is meta-phenylenediamine.

30. A diagnostic kit according to claim 27 wherein the primary, secondary or tertiary aryl amine is para-hydroxyaniline.

31. A diagnostic kit according to claim 22 additionally comprising an oxidising agent.

32. A diagnostic kit according to claim 31 wherein the oxidising agent comprises a copper (II) salt.

33. A diagnostic kit according to claim 31 wherein the oxidising agent comprises a salt selected from the group consisting of an Fe (III), a chromate, a dichromate and a permanganate salt.

34. A diagnostic kit according to claim 22 additionally comprising a base.

35. A diagnostic kit according to claim 34 wherein the base comprises ammonia.

36. A diagnostic kit according to claim 34 wherein the base comprises a base selected from the group consisting of an alkali metal hydroxide, a borate buffer and an alkaline solution of an organic amine.

37. A diagnostic kit according to claim 22 wherein the enzyme is retained on a solid support.

38. A diagnostic kit according to claim 22 wherein the enzyme is dissolved in one or more solvents.

39. A diagnostic kit according to claim 38 wherein at least one of the one or more solvents comprises glycerol.

40. A diagnostic kit according to claim 39 wherein the one or more solvents comprises, in admixture, between 10 and 70% (v/v) glycerol and between 90 and 30% (v/v) water.

41. A diagnostic kit according to claim 22 wherein the organic compound suitable for converting the aniline to an indamine, an indophenol or anindoaniline is dissolved in one or more solvents.

42. A diagnostic kit according to claim 31 wherein the oxidising agent is dissolved in one or more solvents.

43. A diagnostic kit according to claim 34 wherein the base is dissolved in one or more solvents.

44. A diagnostic kit according to claim 43 wherein the solution of the base is combined with a solution of the oxidising agent.

45. A diagnostic kit according to claim 44 wherein the solution of the base, the solution of the oxidising agent and a solution of the organic compound suitable for converting the aniline to an indamine, an indophenol or an indoaniline, are combined.

46. A diagnostic kit according to claim 44 wherein the solvent is water.

* * * * *